United States Patent
Howard (10) Patent No.: US 11,779,143 B2
(45) Date of Patent: Oct. 10, 2023

(54) DISPOSABLE GARMENT AND DONNING SYSTEM

(71) Applicant: National Technology & Engineering Solutions of Sandia, LLC, Albuquerque, NM (US)

(72) Inventor: Panit Clifton Howard, Albuquerque, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 501 days.

(21) Appl. No.: 17/165,996

(22) Filed: Feb. 3, 2021

(65) Prior Publication Data

US 2021/0315402 A1 Oct. 14, 2021

Related U.S. Application Data

(62) Division of application No. 15/966,831, filed on Apr. 30, 2018, now Pat. No. 10,925,424.

(60) Provisional application No. 62/501,223, filed on May 4, 2017.

(51) Int. Cl.
| | |
|---|---|
| A47G 25/90 | (2006.01) |
| A41D 19/00 | (2006.01) |
| A47G 25/80 | (2006.01) |
| A61B 42/40 | (2016.01) |
| A61B 42/50 | (2016.01) |
| A43B 3/16 | (2022.01) |

(52) U.S. Cl.
CPC ....... *A47G 25/904* (2013.01); *A41D 19/0055* (2013.01); *A47G 25/80* (2013.01); *A61B 42/40* (2016.02); *A61B 42/50* (2016.02); *A41D 2400/44* (2013.01); *A41D 2400/52* (2013.01); *A43B 3/163* (2013.01)

(58) Field of Classification Search
CPC ...... A47G 25/904; A47G 25/80; A61B 42/40; A61B 42/50; A41D 19/0055; A41D 2400/44; A41D 2400/52; A43B 3/163
See application file for complete search history.

(56) References Cited

U.S. PATENT DOCUMENTS

| | | | | |
|---|---|---|---|---|
| 2,741,410 | A * | 4/1956 | La Violette | A61B 42/00 223/111 |
| 3,464,588 | A | 9/1969 | Strike et al. | |
| 4,889,266 | A | 12/1989 | Wight | |
| 4,915,272 | A * | 4/1990 | Vlock | B25J 21/02 223/111 |
| 6,708,840 | B2 * | 3/2004 | Grinberg | A47G 25/904 221/34 |

(Continued)

*Primary Examiner* — Tri M Mai
(74) *Attorney, Agent, or Firm* — Mark A. Dodd (57) ABSTRACT

A donning system allows a user to don disposable garments without contaminating the exterior of the garment. The disposable garment is part of a garment package, which also includes a cuff by which the garment is loaded into and dispensed from the donning system. The cuff includes elements whereby multiple garments are simultaneously loaded, but the garments are dispensed and donned one at a time. The donning system can include multiple cartridges allowing the user to don multiple garments simultaneously, such as right and left gloves or shoe covers. The donning system can include multiple chambers allowing the system to dispense garments of different sizes.

20 Claims, 10 Drawing Sheets

(56) References Cited

U.S. PATENT DOCUMENTS

| | | |
|---|---|---|
| 6,832,708 B2 | 12/2004 | Sinai |
| 7,832,019 B1 | 11/2010 | Bhalla |
| 9,038,819 B2 * | 5/2015 | Perelli .................... A47L 13/22 |
| | | 206/205 |
| 9,668,527 B2 * | 6/2017 | Maltese ............. A41D 19/0051 |
| 10,143,529 B2 * | 12/2018 | Gaines .................. A61B 42/40 |
| 2004/0149788 A1 | 8/2004 | Sato |
| 2005/0204452 A1 * | 9/2005 | Yung ..................... A61B 42/00 |
| | | 2/167 |
| 2007/0150996 A1 * | 7/2007 | McCarville ........ A41D 19/0082 |
| | | 2/159 |
| 2013/0098953 A1 * | 4/2013 | Esten ................ A41D 19/0041 |
| | | 223/111 |
| 2017/0273750 A1 | 9/2017 | Gaines et al. |
| 2017/0296281 A1 | 10/2017 | Gaines et al. |

* cited by examiner

DISPOSABLE GARMENT AND DONNING SYSTEM

RELATED APPLICATIONS

This application is a divisional of prior application Ser. No. 15/966,831, filed Apr. 30, 2018, and entitled DISPOSABLE GARMENT AND DONNING SYSTEM, which claims the benefit of U.S. Provisional Application No. 62/501,223, filed May 4, 2017, the entirety of each of which is incorporated herein by reference.

STATEMENT OF GOVERNMENT INTEREST

This invention was made with Government support under Contract No. DE-NA0003525 awarded by the United States Department of Energy/National Nuclear Security Administration. The Government has certain rights in the invention.

TECHNICAL FIELD

The present invention relates to disposable garments, for example disposable gloves, donning systems for use with disposable garments, and methods for donning disposable garments.

BACKGROUND

In many industries it is critical that materials not be contaminated by workers. As a first example, workers in a medical research laboratory need to manipulate samples without contaminating the samples with their own DNA or introducing stray bacteria. As another example, workers in a semiconductor fabrication laboratory need to manipulate wafers without contaminating the wafers with particles. In both examples, if the worker dons gloves but touches the exterior of the gloves with bare hands during the donning process, the gloves may contaminate their work in the described manner. Contamination may also occur due to contaminants introduced by other garments worn by the worker, for example, shoe covers. At least the health care, pharmaceutical, food preparation, and certain manufacturing industries, for example, the aerospace industry, also face possible contamination or infection issues. Thus, there is a need for disposable garments, for example, gloves or shoe covers, that can be donned without the user touching the exterior of the garment. Similarly, there is a need for corresponding donning systems and methods employing such disposable garments. There is also a need for a more user-friendly garment donning system as such a system will encourage users to more frequently change garments when the original garments become contaminated.

SUMMARY

One aspect of the present invention relates to disposable garments, for example, gloves, having cuffs that allow donning of the garment without the need for a user to touch the exterior of the garment. To this end, certain embodiments of the present invention include a cuff that keeps the garment open, thereby allowing the user to don the garment without touching the exterior of the garment. In certain embodiments, the cuff includes one or more break-off elements whereby the donned garment is released from the cuff.

Another aspect of the present invention relates to a donning system employing the cuffed garments just described. Certain embodiments of the donning system employ garment cartridges that have a plurality of the cuffed garments, with the combination of a cuff and garment being termed a garment package. The corresponding donning system advances the garment packages one at a time from the garment cartridge. Certain embodiments of the donning system include a blower that at least partially inflates the garment, thereby simplifying the donning process for a user. This inflation is especially helpful in applications requiring a user to don multiple layers of garments, for example gloves. Multiple layers of garments might be required in applications needing greater tear resistance or higher levels of contamination control. After the user has donned the garment and released the garment from the cuff, certain embodiments of the donning system dispose of the cuff. Certain embodiments of the donning system then advance the next garment package from the garment cartridge. Certain embodiments of the invention automate one or more of these steps using various sensors and controllers.

A donning system in accord with the present invention may optionally include other features. For example, certain embodiments of the donning system include two donning channels. A donning system including two donning channels allows a user to don two garments simultaneously, such as right and left gloves or shoe covers. As another example, certain embodiments of the donning system include multiple garment chambers having different sized garment packages, thereby allowing a single system to dispense garments to users of all sizes, e.g., gloves to users with small, medium, or large hands.

Yet another aspect of the present invention are methods of donning cuffed garments. Embodiments of this method include one or more of the following optional steps in various combinations or orders. These various optional steps include loading a garment cartridge into a donning system, advancing a garment package, at least partially inflating a garment in the advanced garment package, releasing the garment from the corresponding cuff in the garment package, and disposing of the cuff.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the invention, wherein identical reference numerals refer to identical or similar elements or features in different views or embodiments shown in the drawings.

DETAILED DESCRIPTION

Donning System

Various embodiments of the present disclosure relate to a donning system and a method of operating the same. By using a screw drive, a cuff (and corresponding garment), and an advancement gear in the donning system, a garment can be effectively dispensed to a user of the donning system. Other features, such as a garment cartridge, a gas nozzle to inflate a garment, and various sensors, can make the donning system more efficient.

Figure 1:
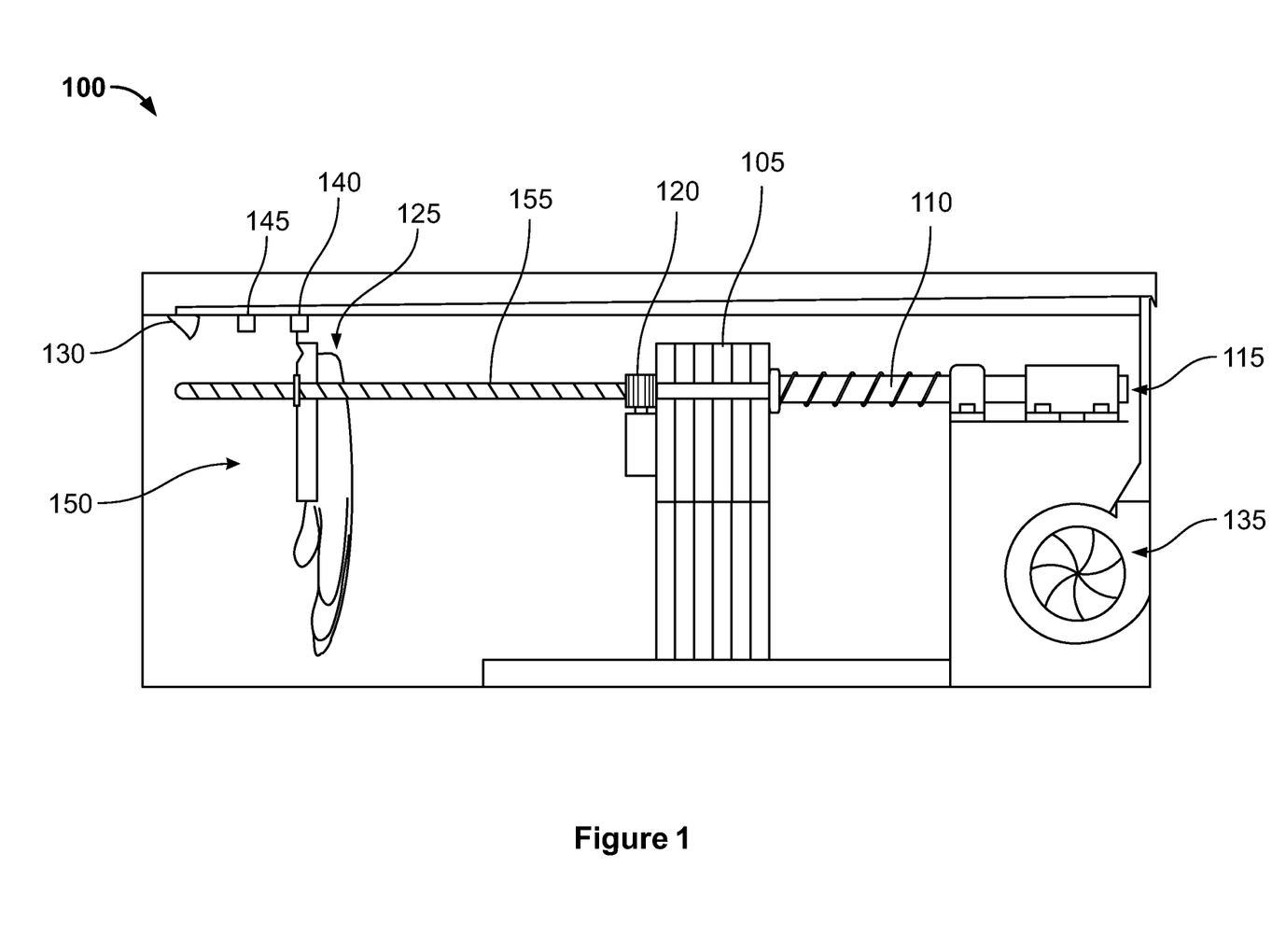
FIG. 1 illustrates a cross-sectional view of a donning system in accordance with one or more embodiments.

FIG. 1 illustrates a cross-sectional view of a donning system 100 in accordance with an embodiment. The donning system 100 includes a garment cartridge 105 loaded onto a screw drive 110. A motor assembly 115 coupled to the screw drive 110 rotates the screw drive 110 as needed. An advancement gear drive 120 engages a garment package 125, as will be described in detail with reference to FIGS. 2 and 3A-3C, in the garment cartridge 105. The donning system 100 includes a gas nozzle 130, a blower 135, a touch sensor 140, and a proximity sensor 145. The various components of the donning system 100 are enclosed within an enclosure 150, which also keeps the garment packages 125 from being contaminated.

During operation, the first cuff and its corresponding garment, i.e., the garment package 125 at the front of the garment cartridge 105, is loaded onto a threaded portion 150 of the screw drive 110 through rotation of the advancement gear drive 120. Portions of the cuff, as will be described in detail with reference to FIGS. 3A-3C, then mesh with the threaded portion 155 of the screw drive 110. The motor assembly 115 rotates the screw drive 110, thereby advancing the garment package 125 towards the front of the enclosure 150. A touch sensor 140 then stops the motor assembly 115 when the garment package 125 reaches a certain point on the threaded portion 155 of the screw drive 110.

A proximity sensor 145 upon detecting, for example a user's hand or foot, causes the gas nozzle 130 to release a stream of pressurized gas, e.g., filtered air, nitrogen, or particulate free gas, into the garment of the garment package 125. The user then inserts, for example, a hand or foot, directly into the garment, allowing the user to avoid having any physical contact with the outside portion of the garment. The user then applies a force to activate one or more break-off elements designed into the cuff, as will be described in detail with reference to FIGS. 3A-3C. This activation force causes the garment to release from its corresponding cuff. The proximity sensor 145 then detects removal of the garment, or, for example, the user's hand or foot, and sends signals to advance the next garment package 125 and to stop the stream of pressurized gas flowing from the gas nozzle 130. In some embodiments, the touch sensor 140, rather than the proximity sensor 145, detects the removal of the garment or the user's hand or foot. In yet other embodiments, the donning system 100 uses both the touch sensor 140 and the proximity sensor 145 to detect removal of the garment or the user's hand or foot.

In some embodiments, rotation of the screw drive 110 to advance the next garment package 125 discharges the now empty cuff from the previous garment package 125 from the screw drive 110. The motor assembly 115 rotates the screw drive 110 advancing the next garment package 125 into position for the user to don the next garment.

The motor assembly 115, which is preferably electrically powered, may in certain embodiments be driven by other power sources. The motor assembly 115 includes one motor in some embodiments, while other embodiments include multiple motors. In various embodiments the motor assembly 115 is operatively coupled to loading screw drive 110 via, for example, one or more, or some combination of: a Da Vinci gear, a belt drive, a pulley, a lever, a linear actuator, a gravity feed, magnetics, a pneumatic rod, a rack and pinion, a ball screw, a scissor jack, or a piston.

In some embodiments, the motor assembly 115 is operatively coupled to the blower 135, which generates the stream of pressurized gas sent to the gas nozzle 130. In other embodiments, the blower 135 includes its own motor for generating the stream of pressurized gas sent to gas nozzle 130. In yet other embodiments, the blower 135 is replaced by a pressurized gas cylinder and a control valve, with the gas selected to minimize possible air-borne contamination.

In some embodiments, the gas nozzle 130 directs multiple streams of pressurized gas. At least one stream of pressurized gas serves to partially inflate the garment, while one or more additional streams of pressurized gas serve to help dry, for example, the user's hand. The reason for these one or more drying streams of pressurized gas is that, for example, gloves may cause the user's hand to sweat. A glove will tend to cling to a wet hand, which makes replacing a glove more difficult. By drying a hand prior to donning the glove, replacing a glove is simplified.

While some embodiments include a proximity sensor 145 to detect, for example, a user's hand or foot, other embodiments may employ a switch. Specifically, embodiments without a proximity sensor 145 may include a switch that a user presses, for example with a hand or foot, that causes the gas nozzle 130 to release a stream of pressurized gas into the garment.

In some embodiments, a proximity sensor 145 is used to turn on one or more ultra-violet (UV) lamps (not illustrated) to bathe the exterior of a garment in UV light. This UV light will help to destroy any bacteria that may be present on the exterior of the garment.

Figure 2A:
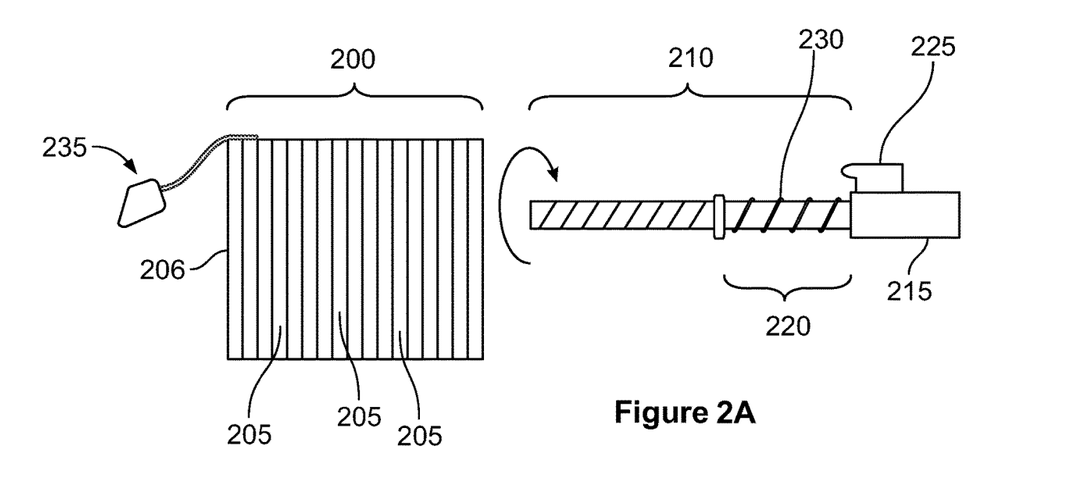
FIG. 2A illustrates a side view of a loaded garment cartridge in accordance with one or more embodiments.

FIG. 2A illustrates a side view of a loaded garment cartridge 200 in accordance with an embodiment. The garment cartridge 200 includes a plurality of garment packages 205. The garment cartridge 200 includes, for example, 50 to 100 garment packages 205. The garment cartridge 200 in various embodiments includes a corresponding plurality of nitrile gloves, latex gloves, shoe covers, covers for various other body parts, or other garments as required by the application.

Each garment package 205 in the garment cartridge 200 includes a corresponding cuff 300, as will be described in detail with reference to FIGS. 3A-3C. In some embodiments, each of the plurality of garment packages 205 includes garments fitting one side of a user, for example, gloves fitting the right hand of a user. In other embodiments, the garment packages alternate between a garment fitting the right side of the user and the left side of the user, for example, gloves fitting first the right hand and then the left hand of the user.

The garment cartridge 200 is loaded into the donning system by placing the garment cartridge 200 on the screw drive 210. The screw drive 210 is then rotated by the motor assembly 215 so that the garment cartridge 200 is driven to the non-threaded portion 220 of the screw drive 210. A stop sensor 225 detects when the garment cartridge 200 is in position on the non-threaded portion 220 of the screw drive 210. During the garment cartridge 200 loading process, the advancement gear drive (not illustrated) can rotate freely so that it does not hinder loading of the garment cartridge 200. Once the garment cartridge 200 is loaded into the donning system 100, a spring 230 biases the garment cartridge 200 against the advancement gear drive (not illustrated), thereby allowing the advancement gear drive to engage the cuff 300 of the first garment package 206.

While some embodiments include a stop sensor 225 to detect the position of the garment cartridge 200, other embodiments may employ a time-based approach. Specifically, embodiments without a stop sensor 225 may cause the motor assembly 215 to drive the screw drive 210 for a time sufficiently long to ensure the garment cartridge 200 is fully driven to the non-threaded portion 220 of the screw drive 210.

Figure 2B:
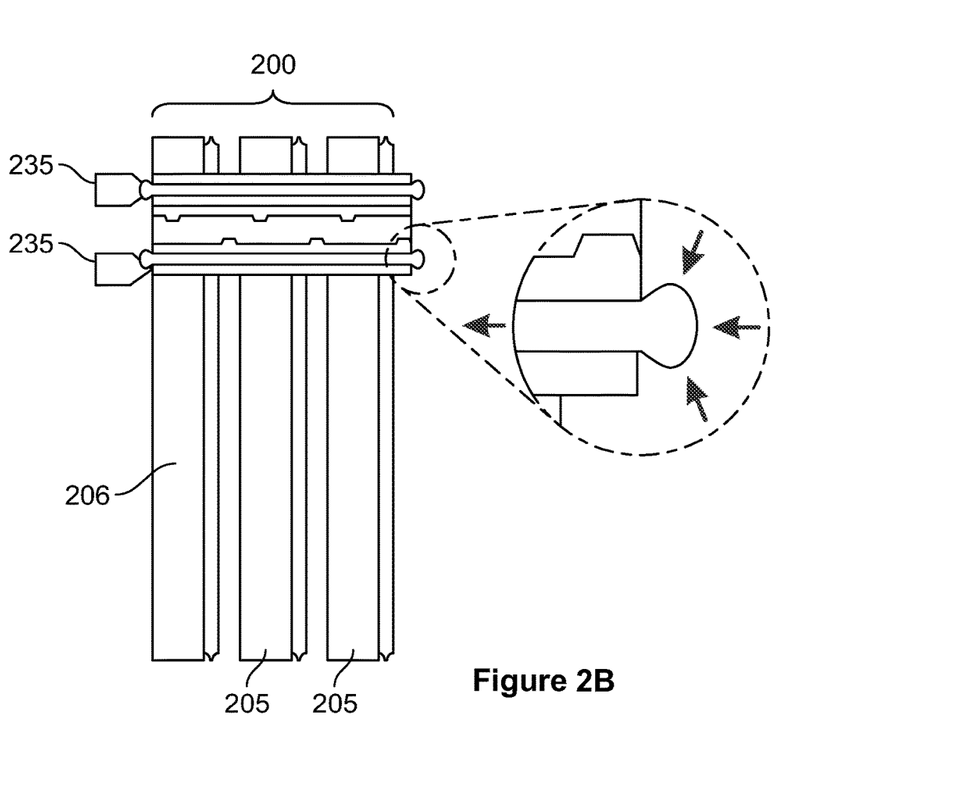
FIG. 2B illustrates an exploded view of the garment cartridge.

To ease loading of the garment cartridge 200, the garment cartridge 200 includes one or more pull tabs 235, as illustrated in FIG. 2B. The one or more pull tabs 235 preferably pass through each of the garment packages 205 in the garment cartridge 200, thereby keeping the garment cartridge 200 intact. Once the garment cartridge 200 has been loaded into the donning system, the one or more pull tabs 235 are pulled and removed from the garment cartridge 200, thereby releasing the individual garment packages 205. After the individual garment packages 205 are released, they are ready for dispensing via the advancement gear drive and the screw drive 210. In some embodiments, engagement pins and corresponding sockets, i.e., male/female connectors, may be used instead of, or in conjunction with, the pull tabs 235 to create the garment cartridge 200.

Cuff

Figure 3A:
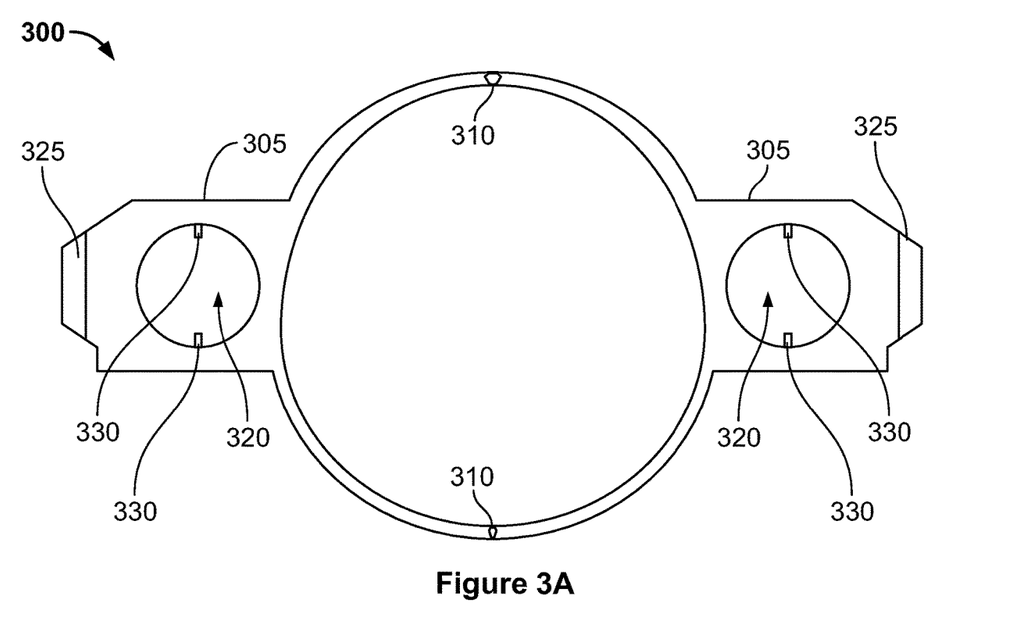
FIG. 3A illustrates a front view of a cuff in accordance with one or more embodiments.

FIG. 3A illustrates a front view of a cuff 300 in accordance with an embodiment as part of a garment package (not illustrated). The cuff 300 includes at least one tab 305 extending from the side of the cuff 300. The cuff 300 also includes at least one break-off element 310. The cuff 300 further includes a garment retention element 315, illustrated in FIG. 3C.

The tab 305 includes both an engagement hole 320 formed through the tab 305 and a tooth 325 formed on an edge of the tab 305. The engagement hole 320 meshes with the screw drive (not illustrated) so that rotation of the screw drive causes the cuff 300, and thus the corresponding garment package (not illustrated), to move along the length of the screw drive. The engagement hole 320 includes one or more knobs 330 that mesh with the screw drive. In other embodiments, the engagement hole 320 includes threads (not illustrated), formed around the periphery of the engagement hole, that mesh with the screw drive.

For embodiments having two or more tabs 305, the tabs 305 are preferably separated by 90 degrees or more, and more preferably separated by 120 degrees or more, about the periphery of the cuff 300 as illustrated in FIG. 3A.

The tooth 325 engages with the advancement gear drive (not illustrated) such that rotation of the advancement gear drive causes the cuff 300 to be moved from the non-threaded portion of the screw drive (not illustrated) to the threaded portion of the screw drive (not illustrated), as will be described in detail with reference to FIGS. 5 and 6. Once the advancement gear drive has moved the cuff 300 from the non-threaded portion of the screw drive to the threaded portion of the screw drive, rotation of the screw drive causes the cuff 300, and thus the corresponding garment package, to move along the length of the screw drive.

In some embodiments with a single tab 305, for example, cuffs for use in a donning system where the screw drive has a single shaft, motion of the cuff 300 and its corresponding garment package along the length of the screw drive may be unstable. To stabilize this motion, the cuff 300, or more preferably the tab 305, can include one or more guide holes (not illustrated). By placing one or more fixed rods, which are substantially parallel to the screw drive, through respective guide holes, any unintended rotation of the cuff 300 causes it to interfere with the fixed rod(s), which apply a counteracting force. Alternatively, the cuff 300, or more preferably the tab 305, can include one or more guide notches (not illustrated). By placing one or more fixed rods, which are substantially parallel to the screw drive, through respective guide notches, the motion of the cuff 300 and its corresponding garment package is similarly stabilized. A combination of guide hole(s) and guide notch(es) may also be employed in the cuff 300.

In other embodiments with a single tab 305, the donning system includes a guide channel (not illustrated) to stabilize motion of the cuff 300 and its corresponding garment package along the length of the screw drive. Specifically, this guide channel, which is substantially parallel to the screw drive, surrounds two, or preferable three, sides of the cuff 300 or the tab 305. By placing the guide channel so that it surrounds two or three sides of the cuff 300 or the tab 305, any unintended rotation of the cuff 300 causes the cuff 300 or the tab 305 to interfere with the guide channel, which applies a counteracting force.

In embodiments with two tabs 305, the cuff 300 preferably includes two break-off elements 310 at different locations about the periphery of the cuff 300. In embodiments with two tabs 305, the cuff 300 preferably includes two break-off elements 310 with each of the break-off elements 310 located about the periphery of the cuff 300 between two tabs 305, as illustrated in FIG. 3A. In embodiments with two tabs 305 and two breakoff elements 310, the break-off elements 310 are more preferably opposite one another about the periphery of the cuff 300, as illustrated in FIG. 3A. Other embodiments may include only a single break-off element 310, while yet other embodiments may include three or more break-off elements 310.

Figure 3B:
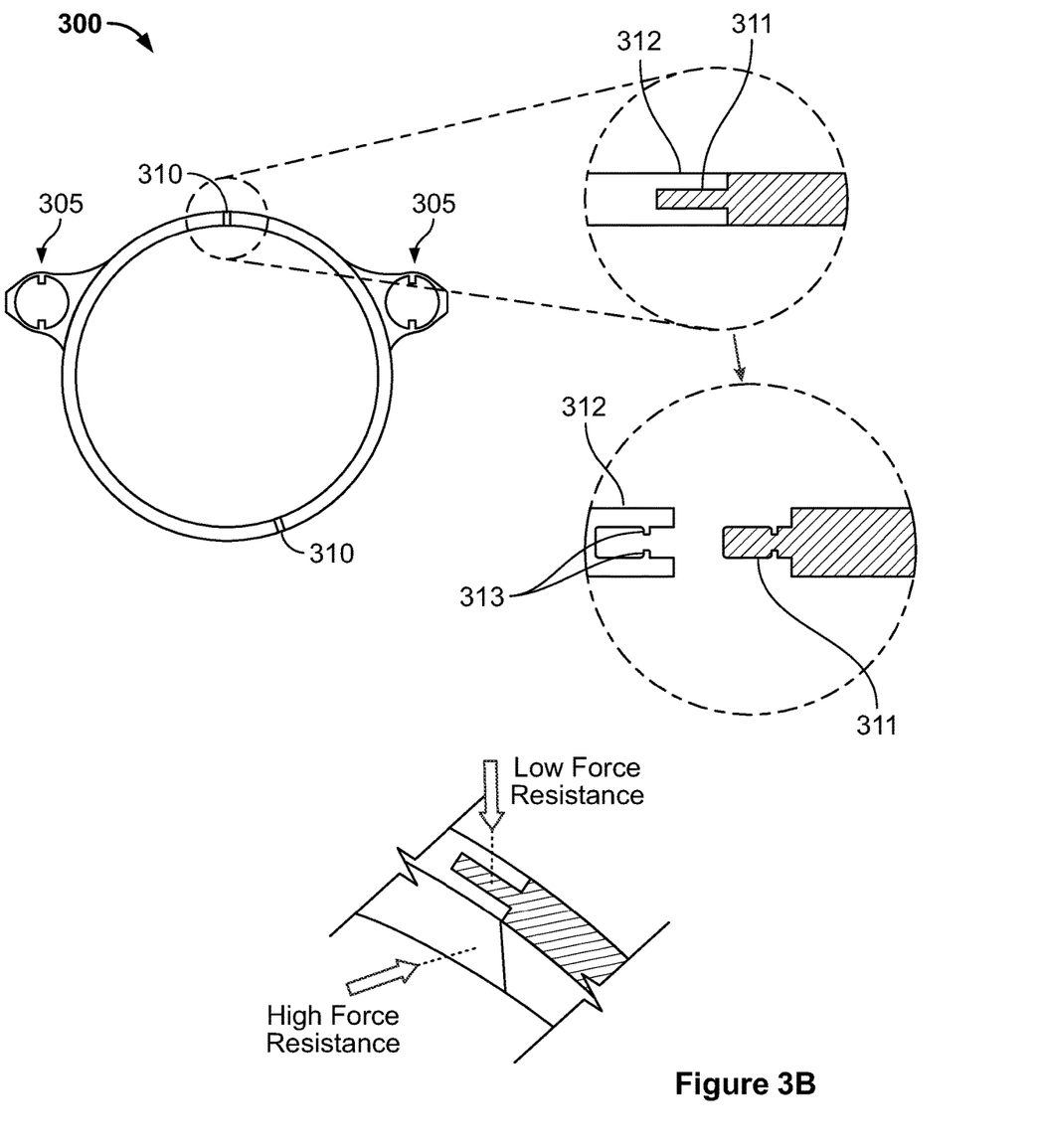
FIG. 3B illustrates a side view of a cuff in accordance with one or more embodiments.

FIG. 3B illustrates an exploded view of a cuff 300 in accordance with an embodiment. As illustrated, break-off element 310 includes a tongue 311 and a corresponding groove 312. The tongue 311 and the groove 312 are sized such that a friction fit is formed when the tongue 311 is inserted in the groove 312. In at least one embodiment, the tongue 311 and the groove 312 have corresponding dimples 313 to form or strengthen the friction fit. A break-off element 310 of this design will withstand a greater force in the direction normal to the opening of the cuff 300, such as when the user is donning the garment, than it will in a direction substantially orthogonal to the opening of the cuff 300, such as when the user applies a force to the cuff to release the garment from the cuff 300. The break-off element 310 is preferably substantially orthogonal to the opening of the cuff 300, as the user applied force is likewise preferably orthogonal to the opening of the cuff 300.

In accordance with another embodiment, the break-off element 310 includes a ball (not illustrated) and a socket (not illustrated). As with the tongue 311 and groove 312 configuration, the socket and the ball, which inserts into the socket, form a friction fit. The ball and socket configuration may also include dimples to form or strengthen the friction fit.

Figure 3C:
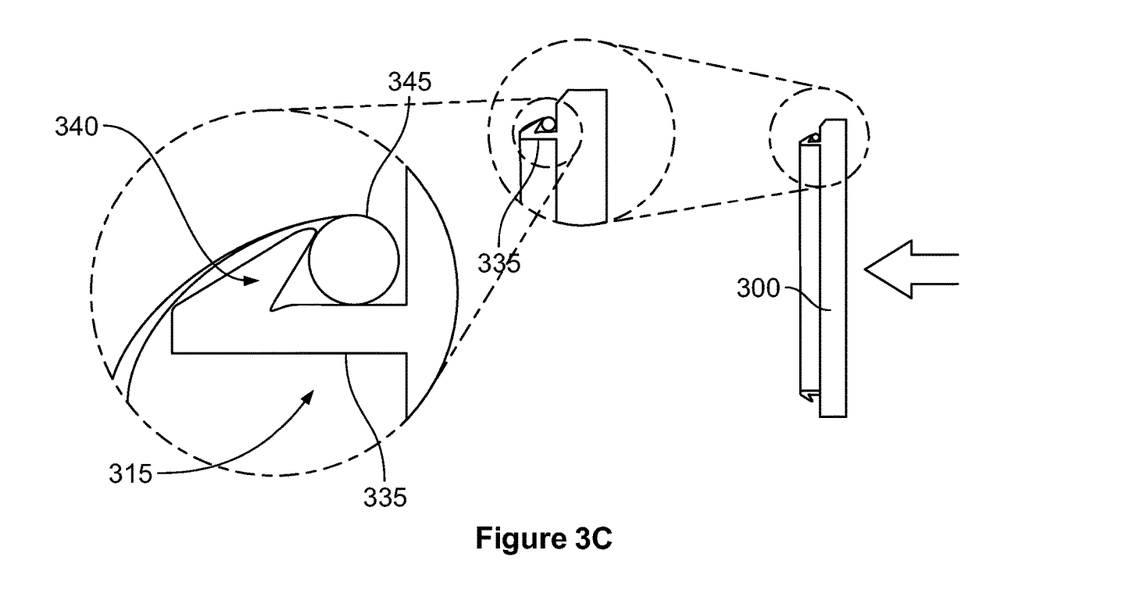
FIG. 3C is an exploded view of a cuff in accordance with one or more embodiments.

FIG. 3C illustrates side and expanded cross-sectional views of a cuff 300 in accordance with an embodiment. The user inserts, for example a hand, in the direction shown by the arrow. The cuff 300 includes garment retention element 315 in the form of a hook 335 with a barb 340. An edge of a garment 345 is retained by the barb 340, forming a friction fit between the edge of the garment 345 and the cuff 300. The hook 335 and barb 340 may surround the entire opening of the cuff 300, or the hook 335 and barb 340 may be formed as segments, with each segment covering only a part of the opening of the cuff 300. In another embodiment, instead of the hook 335 and barb 340 configuration, the cuff 300 employs a groove, as will be described in detail with reference to FIGS. 4A-4B.

The cuff 300 may be made from a polymer, a plastic, a metal, a non-metal, the garment material (though having a greater thickness than in the garment itself), or some combination thereof. The cuff material is preferably substantially more rigid than the garment material.

Figure 4A:
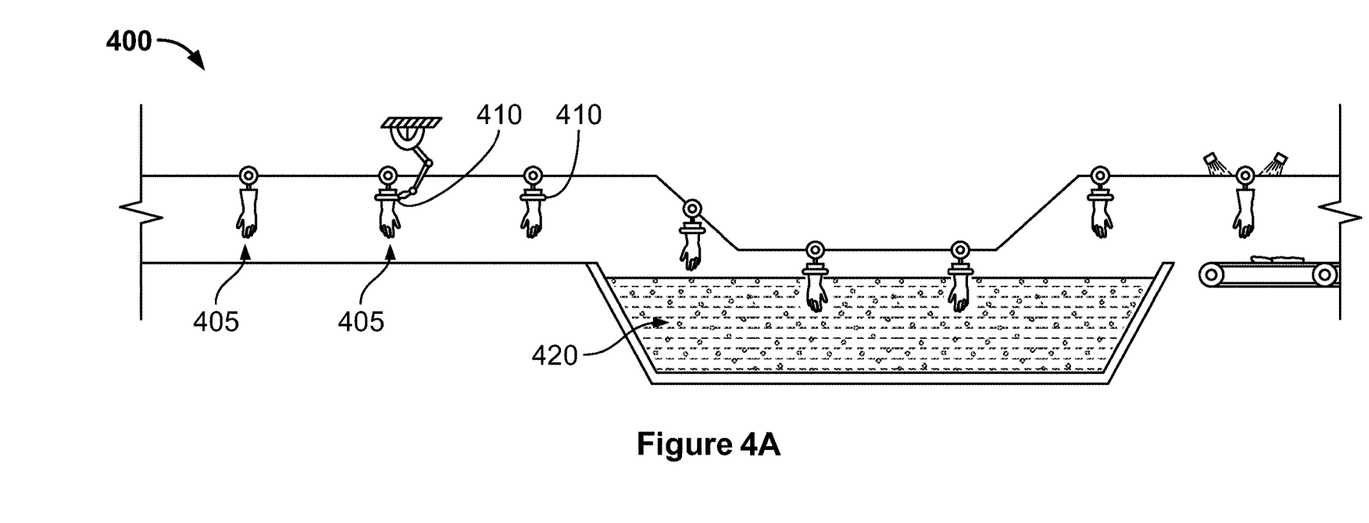
FIG. 4A illustrates a disposable glove assembly line in accordance with one or more embodiments.
Figure 4B:
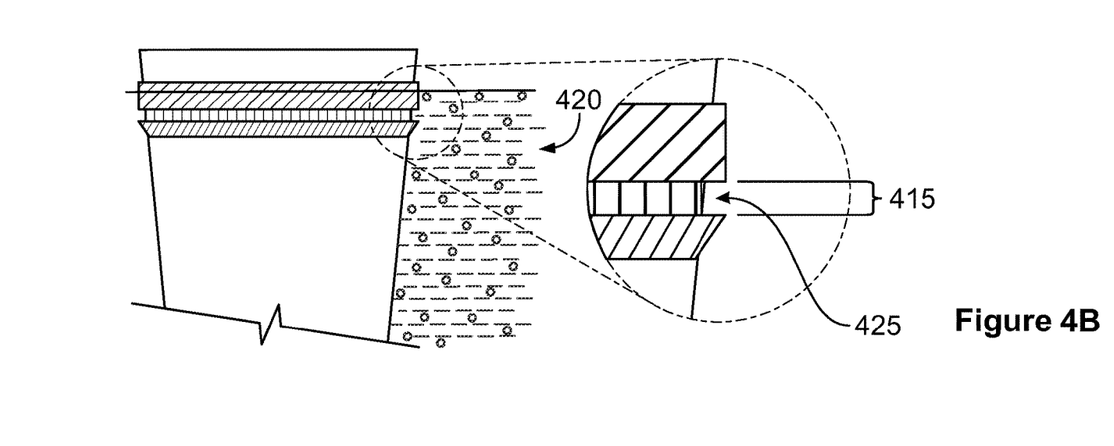
FIG. 4B illustrates an exploded view of the cuff and disposable glove.

FIG. 4A illustrates an assembly line 400 for making a disposable glove and corresponding cuff in accordance with an embodiment. The manufacturing line 400 includes a series of glove molds 405. A cuff 410, with a groove 415 as shown in FIG. 4B, is attached to the glove mold 405 either manually or automatically. The glove mold 405 with corresponding cuff 410 are dipped into a liquid material 420 from which the disposable glove is formed. The liquid material 420 may be, for example, a nitrile- or latex-based liquid, to form nitrile and latex disposable gloves, respectively. As illustrated in FIG. 4B, the liquid material 420 enters the groove 415, thereby forming a retaining ring 425 of the liquid material 420 in the groove 415. This retaining ring 425 of the liquid material 420, when cured, will cause the disposable glove to frictionally fit with the cuff 410 until a user applies enough force to deform the retaining ring 425, thereby separating the disposable glove from the cuff 410. The glove mold 405 with corresponding preformed cuff 410 are then removed from the liquid material 420. The liquid material 420 cures to form the disposable glove and the combined disposable glove and corresponding cuff 410 are released from the glove mold 405.

Disposable Garment and Donning System

As illustrated in FIG. 1, a screw drive 110 advances garments across donning system 100 for users to don. FIG. 5 illustrates a top view of a screw drive 500 in accordance with an embodiment. In FIG. 5, the screw drive 500 includes a first shaft 505 and a second shaft 510. In other embodiments, loading screw drive 500 includes two, or more, pairs of shafts. First shaft 505 includes a first non-threaded portion 506 and a first threaded portion 507, while second shaft 510 includes a second non-threaded portion 511 and a second threaded portion 512. The first and second springs 515, 520 are coiled around the first and second non-threaded portions 506, 512. The first and second shafts 505, 510 are preferably substantially parallel.

In some embodiments, the loading screw drive includes a single shaft with both threaded and non-threaded portions. In other embodiments, such as the one illustrated in FIG. 5, the loading screw drive 500 includes two (or more) shafts 505, 510, each having respective threaded 507, 512 and non-threaded 506, 511 portions. The use of two (or more) shafts 505, 510 may be desirable in applications employing heavier garment cartridges 525 or in applications needing a greater activation force to release the garment from its corresponding cuff. In a screw drive 500 with two shafts 505, 510, the shafts 505, 510 may rotate in the same direction, e.g., both clockwise or both counterclockwise, or in opposite directions, i.e., one clockwise and the other counterclockwise.

To accommodate cuffs of different sizes, and thus their corresponding garment cartridges 525, the spacing between the first and second shafts 505, 510 is, in certain embodiments, variable. For example, the cuff for a small glove is smaller than the cuff for a large glove. Thus, a donning system that dispenses garments of different sizes would benefit from this capability to vary the spacing between the first and second shafts 505, 510.

A garment cartridge 525 is loaded onto screw drive 500. Specifically, a garment cartridge 525 including a plurality of garment packages 530 is placed onto the first and second shafts 505, 510 through corresponding engagement holes (not illustrated) in the cuffs of the garment packages 530. The garment cartridge 525 is driven to the first and second non-threaded portions 506, 511 of the first and second shafts 505, 510, respectively. The first and second springs 515, 520 exert forces that push the garment cartridge 525 toward the first and second threaded portions 507, 512 of the first and second shafts 505, 510, respectively. First and second advancement gears 535, 540 control the advancement of each garment package 530 within the garment cartridge 525 onto the first and second threaded portions 507, 512 of the first and second shafts 505, 510, respectively.

Figure 5:
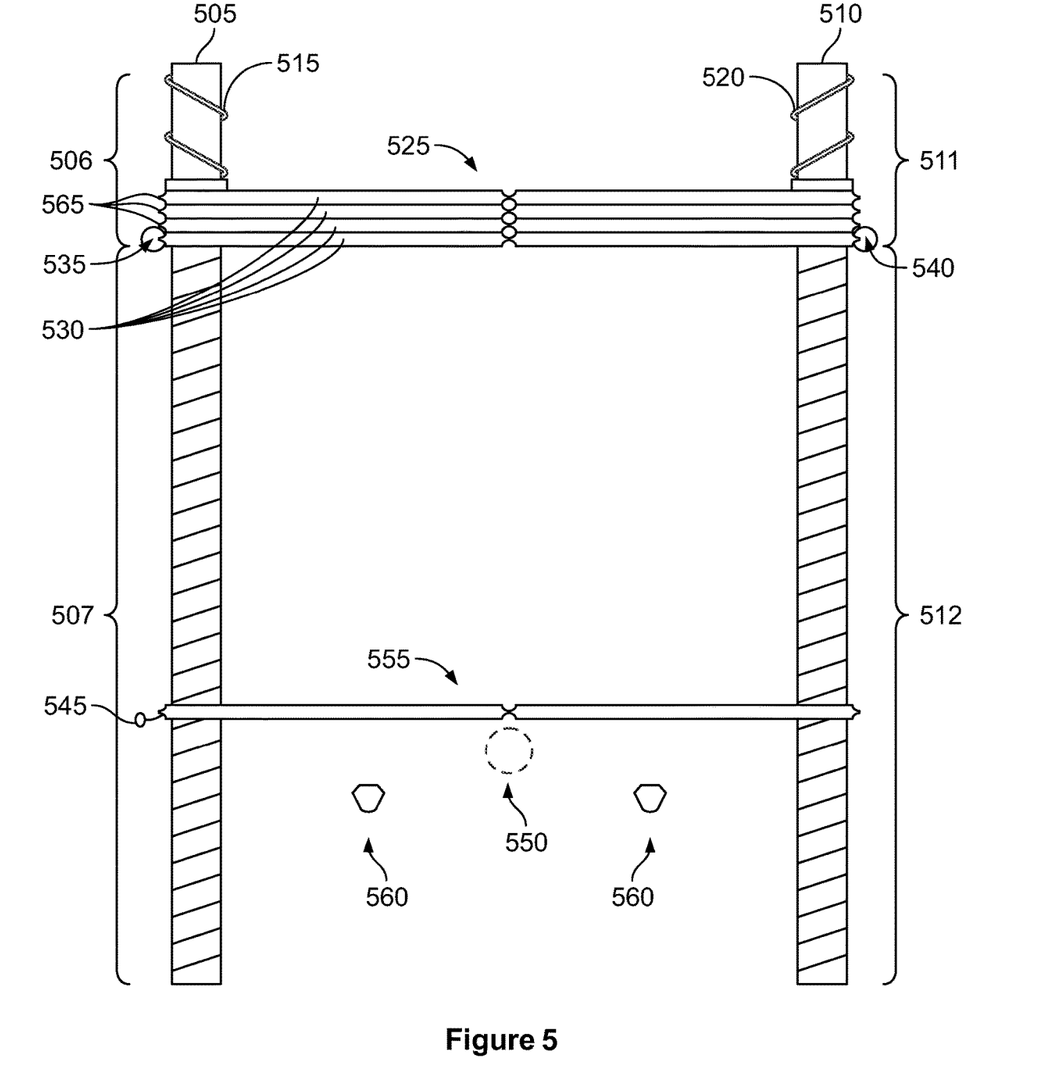
FIG. 5 illustrates a top view of a screw drive in accordance with one or more embodiments.

FIG. 5 illustrates a touch sensor 545 used to determine that a garment package 530 has advanced to the correct point on the screw drive 500. Other embodiments employ a time-based approach. Specifically, embodiments without a touch sensor 545 may cause the motor assembly to drive the screw drive 500 for a predetermined time.

FIG. 5 further illustrates a proximity sensor 550 that determines the presence of, for example, a user's hand or foot. Upon sensing, for example, the user's hand or foot, the proximity sensor causes a blower (not illustrated) to create a stream of pressurized gas directed into the garment ready for donning 555 via gas nozzles 560 to partially inflate the garment 555.

In some embodiments, touch sensor 545 is used to implement a garment package counter functionality. This garment package counter functionality counts the number of individual garment packages 530 when a garment cartridge 525 is loaded into the donning system, for example, by counting the number of teeth 565 that pass the touch sensor 545. The garment package counter functionality also counts the number of individual garment packages 530 as they are dispensed from the donning system, again by counting the number of teeth 565 that pass the touch sensor 545. The information from the garment package counter functionality can be used to display the number of garments in the donning system or to raise a warning when the donning system needs to be reloaded with garments.

Figure 6:
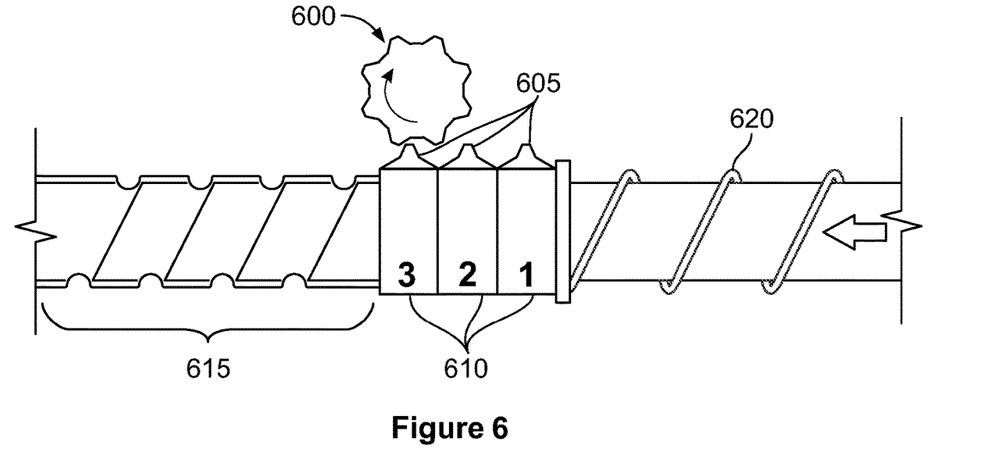
FIG. 6 illustrates a side view of an advancement gear in accordance with one or more embodiments.

FIG. 6 illustrates a side view of the operation of an advancement gear 600 in accordance with an embodiment. As illustrated, the advancement gear 600 meshes with a tooth 605 of a cuff 610 to a corresponding garment package closest to a threaded portion of a shaft of a screw drive 615. A spring 620 exerts a force that pushes the cuffs 610 and corresponding garment packages toward the threaded portion of the shaft of the screw drive 615 so that the next garment package is ready for advancing. In embodiments employing a cuff 610 with multiple tabs (305, FIG. 3A), the corresponding donning systems may employ a single advancement gear 600 or multiple advancement gears 600, preferably with one advancement gear 600 for each tab (305, FIG. 3A) of the cuff 610. For example, FIG. 5 illustrates an embodiment of a donning system that employs a garment package 530 having a cuff (300, FIG. 3A) with two tabs (305, FIG. 3A) and corresponding teeth (325, FIG. 3A), and thus employs first and second advancement gears 535, 540.

In some embodiments, the advancement gear drive (120, FIG. 1) coupled to advancement gear 600 includes garment package counter functionality. The garment package counter functionality counts the number of individual garment packages when a garment cartridge is loaded into the donning system (100, FIG. 1). For example, the garment package counter functionality may count the number of rotations of the advancement gear 600 induced by the passage of the teeth 605 of the loaded garment packages. The garment package counter functionality also counts the number of individual garment packages as they are dispensed from the donning system. For example, the garment package counting functionality may again count the number of rotations of the advancement gear 600 induced by the passage of the teeth 605 of the dispensed garment packages. The information from the garment package counter functionality can be used to display the number of garment packages in the donning system, or used to raise a warning when the donning system needs to be reloaded with garments.

Figure 7A:
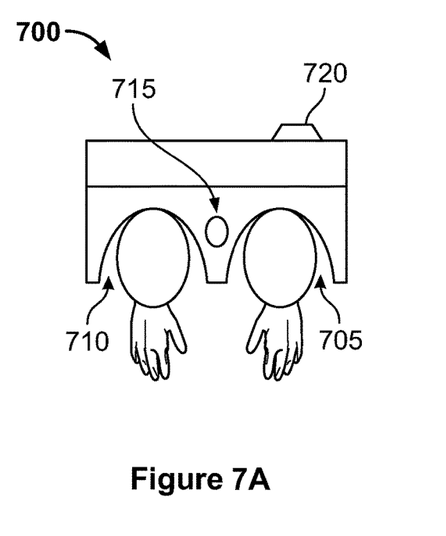
FIG. 7A illustrates a front view of a donning system enclosure in accordance with one or more embodiments.

FIG. 7A illustrates a front view of an enclosure 700 according to an embodiment. The enclosure 700 includes right and left windows 705, 710 for insertion of a user's right and left hands, respectively. In other embodiments, a user would insert right and left feet into the right and left windows 705, 710, respectively. The enclosure 700 includes a sensor 715 that generates a signal causing the right and left windows 705, 710 to automatically open when a user's presence is detected. In other embodiments, the user presses a button to open the right and left windows 705, 710. In yet other embodiments, the user manually opens the right and left windows 705, 710. The enclosure includes a display 720 that displays relevant information. This relevant information may include, for example, the number of garments remaining in the donning system or a warning when the number of remaining garments falls below a specified threshold, i.e., when the donning system needs to be reloaded with garments. With the exception of the right and left windows 705, 710, the enclosure 700 is sealed.

Figure 7B:
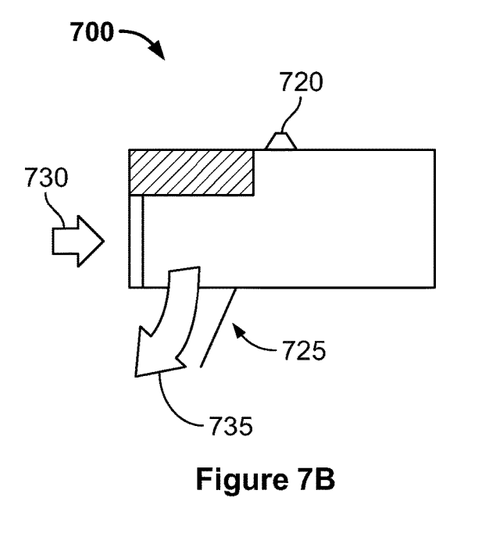
FIG. 7B illustrates a side view of a donning system enclosure in accordance with one or more embodiments.

FIG. 7B illustrates a side view of the enclosure 700 according to an embodiment. The enclosure 700 includes a door 725 configured to open when a cuff (300, FIG. 3A) is discharged from the screw drive (110, FIG. 1), i.e., after the user has donned the garment corresponding to the cuff (300, FIG. 3A). Arrow 730 shows the direction of, for example, a user's hand for donning a glove. Arrow 735 shows the direction of, for example, the user's hand after donning the glove, with the user applying a generally downward force to release the glove from its corresponding cuff. In other embodiments, the user may apply an upward or lateral force to release the glove from its corresponding cuff. In some embodiments, the door 725 opens automatically based upon a signal from the touch sensor (140, FIG. 1) or the proximity sensor (145, FIG. 1). In other embodiments, the user opens the door 725 manually. Below the door 725 is placed a bin (not illustrated) for collecting the discharged cuff (300, FIG. 3A) and later disposal or recycling thereof.

The enclosure 700 includes a lid 730 coupled to an open/close switch. A user opens the lid 730 to install a garment cartridge (105, FIG. 1) onto the screw drive (110, FIG. 1). Upon closing the lid, the open/close switch generates a signal causing the motor assembly (115, FIG. 1) to rotate the screw drive (110, FIG. 1), thereby moving the garment cartridge (105, FIG. 1) to the back of the enclosure 700.

Figure 8A:
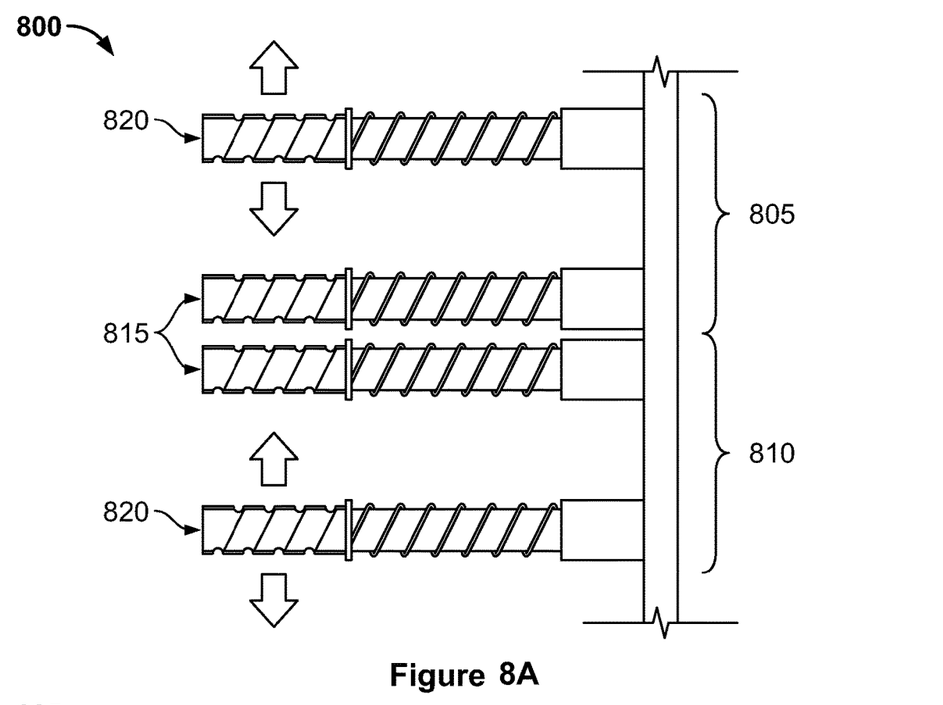
FIGS. 8A and 8B illustrate top and end views, respectively, of a donning system in accordance with one or more embodiments.

FIG. 8A illustrates a top view of a donning system 800 in accordance with an embodiment. The donning system 800 includes first and second screw drives 805, 810. The two center-most shafts 815 are static, while the two outer-most shafts 820 can be adjusted so that the distance between the center-most shafts 815 and their corresponding outer-most shafts 820 can be varied. By varying the distance between the inner-most shafts 815 and their corresponding outer-most shafts 820, different size garments, with their correspondingly different size cuffs, may be dispensed.

As an alternative, in some embodiments, the design of the cuff changes for different size garments rather than requiring the above described change in the distance between the shafts of the screw drive. Specifically, the spacing between the engagement holes remains constant, but the size of the cuff opening through which, for example, the user places a hand, varies. For small garments, the cuff opening would be smaller than the cuff opening for large garments. To balance the change in cuff opening sizes, the length of the tabs would also be changed. Thus, cuffs with small cuff openings would require longer tabs to keep the same engagement hole and shaft spacing relative to cuffs with large cuff openings, which would require correspondingly shorter tabs.

Figure 8B:
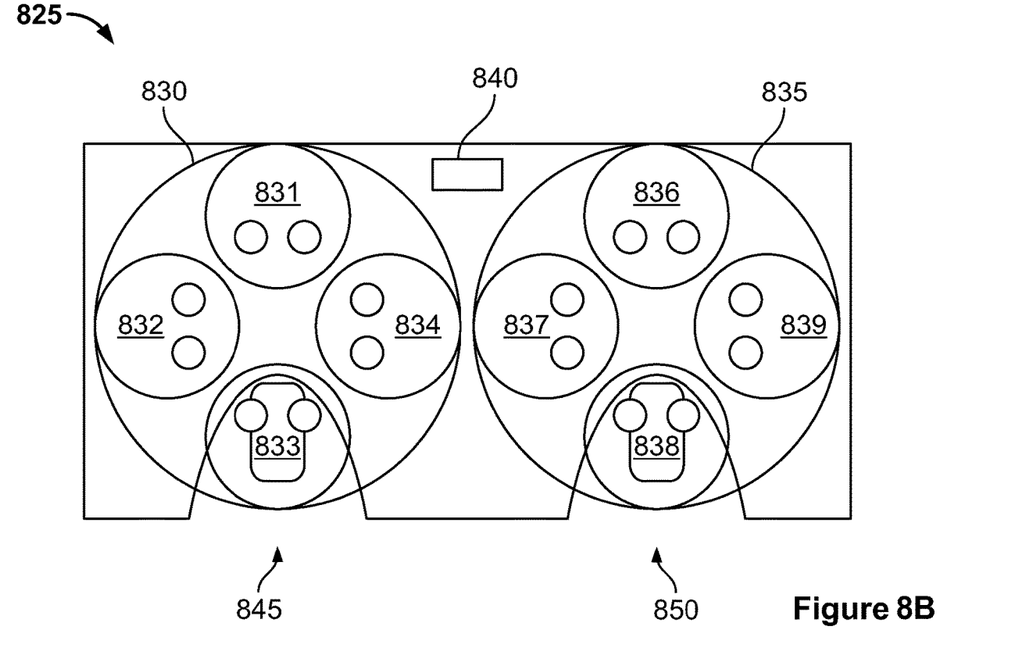

FIG. 8B illustrates an end view of a donning system 825 in accordance with an embodiment. The donning system 825 includes first and second cylinders 830, 835. The first and second cylinders 830, 835 each include four corresponding chambers 831-834, 836-839. Each of the chambers 831-834, 836-839 preferably dispense garments of different sizes. For example, chambers 831 and 836 dispense small garments, chambers 832 and 837 dispense medium garments, chambers 833 and 838 dispense large garments, and chambers 834 and 839 dispense extra-large garments. The donning system 825 includes a selector switch 840 through which a user selects the desired garment size. Upon the user selecting a garment size via the selector switch 840, the donning system 825 causes the first and second cylinders 830, 835 to rotate so the selected size garment is available for donning through first and second windows 845, 850. In some embodiments, the donning system 825 includes an RFID tag reader that senses an RFID tag worn by the user. The RFID tag reader determines the user's garment size based upon information stored in the user's RFID tag and causes the donning system 825 to automatically rotate and dispense the correct garment size.

While the embodiment illustrated in FIG. 8B has first and second windows 845, 850 located on the bottom of the donning system 825 for use with cuffs requiring a downward movement to separate the garments from their cuffs, other embodiments may include first and second windows 845, 850 located on the sides or the top of donning system 825 for use with cuffs requiring corresponding lateral or upward movement to separate the garments from their cuffs.

While the embodiment illustrated in FIG. 8B has four chambers 831-834, 836-839 in each of the first and second cylinders 830, 835, respectively, other embodiments may include two, three, or more than four chambers in the first and second cylinders 830, 835 depending upon the application of the donning system 825.

While the embodiment illustrated in FIG. 8B has four chambers 831-834 each loaded with different size garments, other embodiments may dispense the same size garments from all four chambers 831-834. The embodiments that dispense the same size garments from all four chambers 831-834 could be used in applications that demand many users to don garments in rapid succession, for example during a shift change. In these applications, taking time to reload the donning system with garment cartridges during a shift change may not be practical.

Donning System Method

Figure 9:
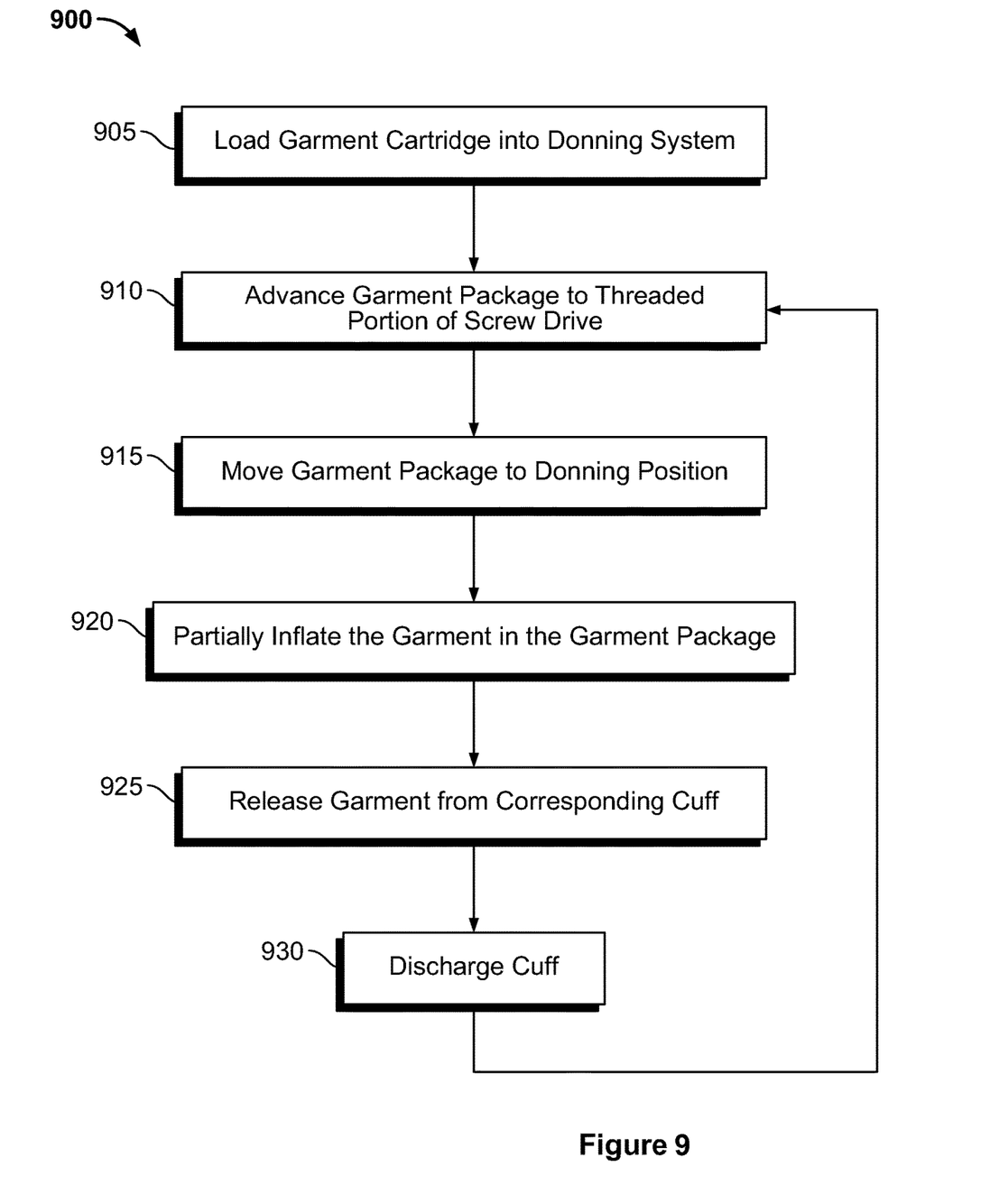
FIG. 9 is a flow chart of a method of operating a donning system in accordance with one or more embodiments.

FIG. 9 illustrates a flow chart of a method of operating a donning system 900 in accordance with an embodiment. In step 905 a garment cartridge is loaded into a donning system. For example, each shaft of a screw drive is inserted into a corresponding engagement hole of the cuffs within the garment cartridge. Each shaft of the screw drive rotates to allow knobs or threads within the engagement holes to mesh with a threaded portion of the shaft during loading.

Next, each tooth of each cuff within a garment cartridge rotates an advancement gear of an advancement gear drive after moving across the threaded portions of the shafts of the screw drive. When the garment cartridge is fully moved into position, pressure from one or more springs holds the tooth of the cuff of the first garment package in the garment cartridge against the advancement gear drive. The pull tabs of the garment cartridge are then removed, thereby allowing the individual garment packages within the garment cartridge to separate.

In step 910, a garment package is advanced onto the threaded portions of the shafts of the screw drive. For example, the advancement gear for each shaft rotates, thereby engaging a corresponding tooth on the cuff of the garment package and advancing the garment package onto the threaded portions of corresponding shafts of the screw drive. The engagement holes of the cuff of the garment package, with their knobs or threads, now mesh with the threaded portions of the corresponding shafts of the screw drive.

Figure 10:
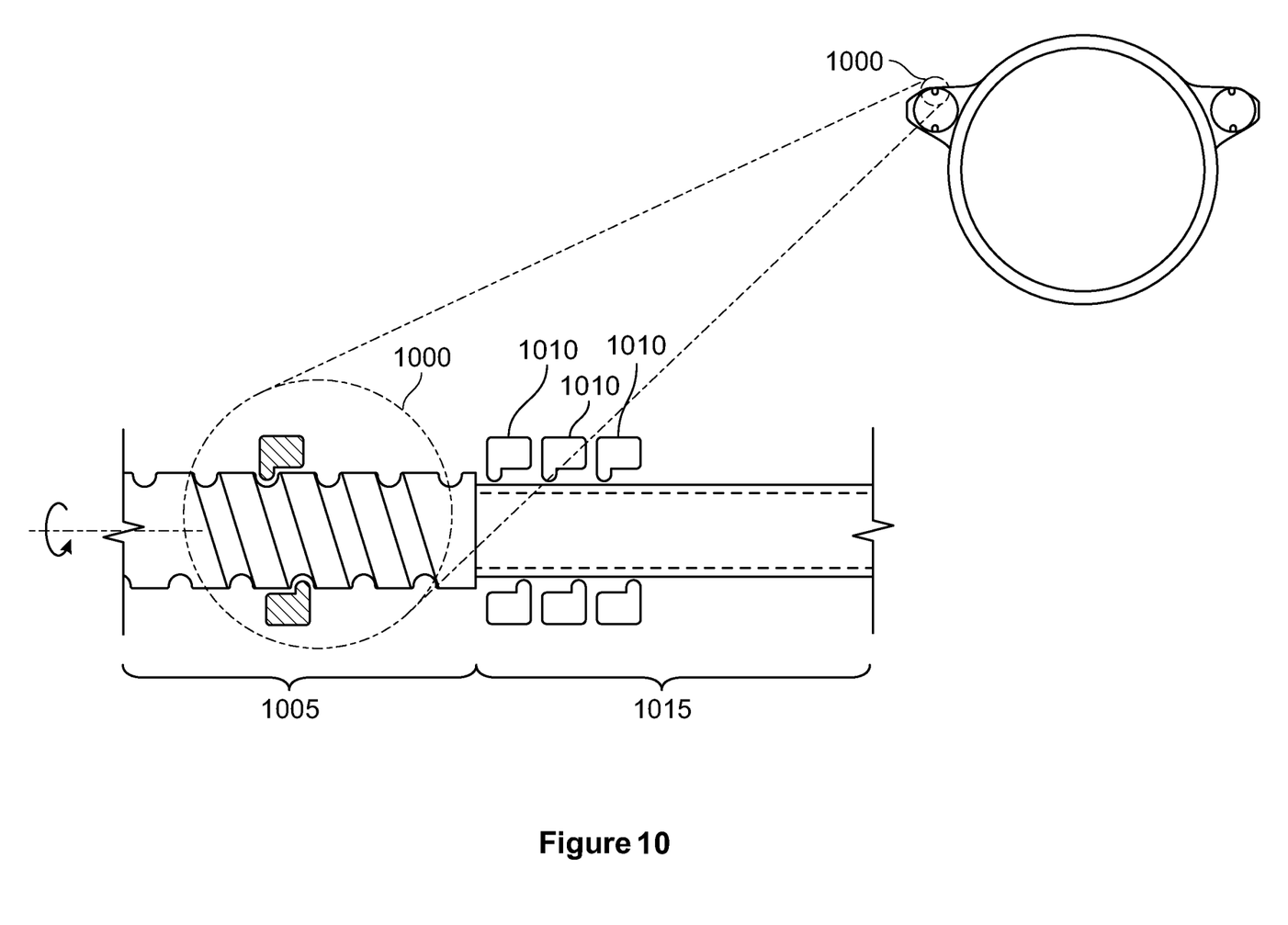
FIG. 10 illustrates a cross-sectional view of a garment package across a threaded portion of a screw drive in accordance with one or more embodiments.

In step 915, a garment package is moved across the threaded portions of the shafts of the screw drive to the donning position. For example, after the engagement holes of the cuff of the garment package mesh with the threaded portions of the corresponding shafts of the screw drive, a motor assembly rotates each shaft of the screw drive to move the garment package across the threaded portion of the shafts of the screw drive until the garment package reaches the donning position. FIG. 10 illustrates a cross-sectional view of a cuff of a garment package 1000 starting to be moved across the threaded portion of a shaft 1005. FIG. 10 further illustrates cuffs of additional garment packages 1010 on the non-threaded portion of the shaft 1015.

In step 920, a garment of a garment package is inflated with pressurized gas. For example, the garment package, upon reaching the donning position on the threaded portion of the screw drive, touches a touch sensor. The touch sensor causes the motor assembly to stop rotating the shafts of the screw drive, thereby stopping motion of the garment package. The user then places a body part, for example, a hand or foot, in proximity to the garment, thereby triggering a proximity sensor. The proximity sensor activates a blower causing a stream of gas to blow out a gas nozzle to at least partially inflate the garment with pressurized gas.

In step 925, a garment of a garment package is released from the corresponding cuff of the garment package. For example, after donning the garment, the user activates the break-off elements of the cuff by applying a force to the cuff.

In step 930, a cuff of a garment package is discharged from the shafts of the screw drive. For example, the proximity sensor detects the donning and removal of the garment and sends a signal to provide the next garment package, i.e., the method returns to step 910. As the shafts of the screw drive rotate to provide the next garment package, this rotation eventually discharges the now empty cuff from the preceding garment package from the screw drive.

One of ordinary skill in the art will understand that steps may be added, removed, or reordered from the method 900.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A garment package comprising:
   a cuff, the cuff including:
      at least one tab;
      at least one engagement hole, each of the at least one engagement holes formed through a respective one of the at least one tabs;
      at least one tooth, each of the at least one teeth formed on an end of a respective one of the at least one tabs; and
      at least one break-off element; and
   a garment attached to the cuff;
   wherein each of the at least one engagement holes is adapted to mesh with a threaded portion of a respective shaft;
   wherein each of the at least one break-off elements is adapted to withstand a greater force in a first direction than in a second direction, the second direction orthogonal to the first direction; and
   wherein the garment is adapted to detach from the cuff.

2. The garment package of claim 1, wherein the at least one tab is two tabs.

3. The garment package of claim 2, wherein the two tabs are separated by 90 degrees or more about a periphery of the cuff.

4. The garment package of claim 1, wherein the at least one break-off element is two break-off elements.

5. The garment package of claim 4, wherein the two break-off elements are located opposite one another about the periphery of the cuff.

6. The garment package of claim 1 further comprising at least one threaded region, each of the at least one threaded regions being formed around a periphery of a respective one of the at least one engagement holes.

7. The garment package of claim 1 further comprising at least one knob, each of the at least one engagement holes having at least one of the at least one knobs formed on a respective periphery thereof.

8. The garment package of claim 1, wherein each of the at least one break-off elements includes:
   a tongue; and
   a groove;
   wherein the tongue is adapted to frictionally fit in the groove.

9. The garment package of claim 1, wherein each of the at least one break-off elements includes:
   a ball; and
   a socket;
   wherein the ball is adapted to frictionally fit in the socket.

10. The garment package of claim 1,
wherein the cuff further includes at least one hook, the at least one hook around a periphery of the cuff; and
wherein the garment is adapted to be attached to the cuff using the at least one hook.

11. The garment package of claim 1,
wherein the cuff further includes at least one groove, the at least one groove around a periphery of the cuff; and
wherein the garment is adapted to be attached to the cuff using the at least one groove.

12. The garment package of claim 1, wherein the garment is a glove or a shoe cover.

13. A garment cartridge comprising:
a plurality of cuffs, each of the plurality of cuffs including:
at least one tab;
at least one engagement hole, each of the at least one engagement holes formed through a respective one of the at least one tabs;
at least one tooth, each of the at least one teeth formed on an end of a respective one of the at least one tabs; and
at least one break-off element; and
a garment attached to the cuff;
wherein each of the at least one engagement holes is adapted to mesh with a threaded portion of a respective shaft;
wherein each of the at least one break-off elements is adapted to withstand a greater force in a first direction than in a second direction, the second direction orthogonal to the first direction; and
wherein the garment is adapted to detach from the cuff.

14. The garment package of claim 13, wherein the at least one tab is two tabs, the two tabs being separated by 90 degrees or more about a periphery of the cuff.

15. The garment package of claim 13, wherein the at least one break-off element is two break-off elements, the two break-off elements being located opposite one another about the periphery of the cuff.

16. The garment package of claim 13 further comprising at least one threaded region, each of the at least one threaded regions being formed around a periphery of a respective one of the at least one engagement holes.

17. The garment package of claim 13 further comprising at least one knob, each of the at least one engagement holes having at least one of the at least one knobs formed on a respective periphery thereof.

18. The garment package of claim 13, wherein each of the at least one break-off elements includes one of:
a tongue and groove element, the tongue being adapted to frictionally fit in the groove; or
a ball and socket element, the ball being adapted to frictionally fit in the socket.

19. The garment package of claim 13 further comprising at least one pull tab, the garment package adapted to release the plurality of cuffs from one another when the at least one pull tab is removed from the garment package.

20. The garment package of claim 13, wherein each of the plurality of cuffs further includes:
an engagement pin, the engagement pin on a first face of a corresponding one of the plurality of cuffs; and
an engagement socket, the engagement socket on a second face of a corresponding one of the plurality of cuffs opposite the first face;
wherein the plurality of cuffs is adapted to remain aligned due to the engagement pin and the engagement socket.

* * * * *